US010961473B2

(12) United States Patent
Scott

(10) Patent No.: US 10,961,473 B2
(45) Date of Patent: Mar. 30, 2021

(54) PROCESS FOR PRODUCING BIODIESEL AND RELATED PRODUCTS

(71) Applicants: Argent Energy (UK) Limited, North Lanarkshire (GB); Argent Energy Limited, London (GB)

(72) Inventor: Michael Scott, North Lanarkshire (GB)

(73) Assignee: Argent Energy (UK) Limited, Argent Engery Limited, North Lanarkshire (GB)

( * ) Notice: Subject to any disclaimer, the term of this patent is extended or adjusted under 35 U.S.C. 154(b) by 37 days.

(21) Appl. No.: 15/693,655

(22) Filed: Sep. 1, 2017

(65) Prior Publication Data

US 2017/0362521 A1 Dec. 21, 2017

Related U.S. Application Data

(62) Division of application No. 14/897,936, filed as application No. PCT/GB2014/051876 on Jun. 19, 2014, now Pat. No. 10,323,197.

(30) Foreign Application Priority Data

Jun. 19, 2013 (GB) .................................... 1310960
Jun. 19, 2013 (GB) .................................... 1310961
Jun. 19, 2013 (GB) .................................... 1310962

(51) Int. Cl.
*C10L 1/02* (2006.01)
*C11B 3/00* (2006.01)
(Continued)

(52) U.S. Cl.
CPC .............. *C10L 1/026* (2013.01); *C07C 67/03* (2013.01); *C07C 67/08* (2013.01); *C07C 67/58* (2013.01);
(Continued)

(58) Field of Classification Search
CPC ......... C07C 69/24; C07C 69/52; C07C 67/03; C07C 67/08; C07C 67/58; C10L 1/026; C10L 2200/0446; C10L 2200/0476; C10L 2270/026; C10L 2270/04; C10L 2290/06; C10L 2290/18; C10L 2290/542; C10L 2290/543; C10L 2290/544;
(Continued)

(56) References Cited

U.S. PATENT DOCUMENTS 3,428,660 A 2/1969 Morren
3,519,662 A 7/1970 Gruver, Jr. et al.
(Continued)

FOREIGN PATENT DOCUMENTS

CN 101760263 6/2010
CN 102492494 6/2012
(Continued)

*Primary Examiner* — Latosha Hines
(74) *Attorney, Agent, or Firm* — Dorton & Willis LLP; Ryan Willis

(57) ABSTRACT

There is described a process for producing biodiesel and related products from mixtures. There is also described a process for producing precursors and feedstock materials for producing biodiesel and related products. The processes use esterification and trans-esterification, separation and purification. Other process steps such as acidification and distillation can also be used.

10 Claims, 2 Drawing Sheets

(51) Int. Cl.

| | | |
|---|---|---|
| *C11C 3/00* | (2006.01) | |
| *C11B 3/04* | (2006.01) | |
| *C11C 3/10* | (2006.01) | |
| *C07C 67/03* | (2006.01) | |
| *C07C 67/08* | (2006.01) | |
| *C07C 67/58* | (2006.01) | |
| *C11B 3/16* | (2006.01) | |
| *C10G 33/00* | (2006.01) | |
| *C10G 3/00* | (2006.01) | |
| *C11B 3/12* | (2006.01) | |
| *B01D 21/26* | (2006.01) | |
| *B03D 1/14* | (2006.01) | |

(52) U.S. Cl.
CPC ............... *C10G 3/00* (2013.01); *C10G 3/40* (2013.01); *C10G 33/00* (2013.01); *C11B 3/001* (2013.01); *C11B 3/006* (2013.01); *C11B 3/008* (2013.01); *C11B 3/04* (2013.01); *C11B 3/12* (2013.01); *C11B 3/16* (2013.01); *C11C 3/003* (2013.01); *C11C 3/10* (2013.01); *B01D 21/262* (2013.01); *B03D 1/1431* (2013.01); *C10G 2300/1003* (2013.01); *C10G 2300/201* (2013.01); *C10G 2400/04* (2013.01); *C10L 2200/0446* (2013.01); *C10L 2200/0476* (2013.01); *C10L 2270/026* (2013.01); *C10L 2270/04* (2013.01); *C10L 2290/06* (2013.01); *C10L 2290/18* (2013.01); *C10L 2290/542* (2013.01); *C10L 2290/543* (2013.01); *C10L 2290/544* (2013.01); *C10L 2290/547* (2013.01); *Y02E 50/10* (2013.01); *Y02P 30/20* (2015.11)

(58) Field of Classification Search
CPC .... C10L 2290/547; Y02E 50/13; Y02P 30/20; B01D 21/262; B03D 1/1431; C11C 3/003; C11C 3/10; C10G 33/00; C10G 3/00; C10G 3/40; C10G 2300/1003; C10G 2300/201; C10G 2400/04; C11B 3/001; C11B 3/006; C11B 3/008; C11B 3/16; C11B 3/04; C11B 3/12; C11B 3/003; C11B 3/10

See application file for complete search history.

(56) References Cited

U.S. PATENT DOCUMENTS

| | | | |
|---|---|---|---|
| 4,364,743 A | 12/1982 | Erner | |
| 6,822,105 B1 | 11/2004 | Luxem et al. | |
| 7,622,600 B1 * | 11/2009 | Marr | C11C 3/10 554/161 |
| 2005/0232956 A1 | 10/2005 | Bist | |
| 2006/0070912 A1 | 4/2006 | Khan | |
| 2006/0293533 A1 * | 12/2006 | Iyer | C07C 67/03 554/174 |
| 2007/0196250 A1 | 8/2007 | Leveson | |
| 2007/0232817 A1 | 10/2007 | Pereira et al. | |
| 2007/0261294 A1 * | 11/2007 | Aiken | C10L 1/026 44/307 |
| 2009/0030219 A1 | 1/2009 | Su | |
| 2010/0059450 A1 | 3/2010 | Lafosse et al. | |
| 2010/0059451 A1 | 3/2010 | Gallo et al. | |
| 2010/0087671 A1 | 4/2010 | Lemke | |
| 2010/0202933 A1 * | 8/2010 | Iyer | C07C 67/03 422/140 |
| 2010/0228042 A1 * | 9/2010 | Chun | C07C 67/08 554/162 |
| 2010/0242346 A1 * | 9/2010 | Bunning | C07C 67/08 44/388 |
| 2010/0305346 A1 * | 12/2010 | Hara | C11C 3/003 554/170 |
| 2010/0330615 A1 | 12/2010 | Neto | |
| 2011/0023353 A1 | 2/2011 | Ciciulla | |
| 2011/0166378 A1 * | 7/2011 | Pelly | C11C 1/08 560/129 |
| 2011/0192076 A1 | 8/2011 | Hess et al. | |
| 2011/0197497 A1 | 8/2011 | Jiang | |
| 2012/0123140 A1 | 5/2012 | Jackam et al. | |
| 2012/0183354 A1 | 7/2012 | Redmile-Gordon et al. | |
| 2014/0020282 A1 | 1/2014 | Lavella, Sr. | |
| 2014/0275612 A1 * | 9/2014 | Slade | C07C 67/08 560/204 |

FOREIGN PATENT DOCUMENTS

| | | |
|---|---|---|
| CN | 102585927 | 7/2012 |
| CN | 103571630 | 2/2014 |
| FR | 2894977 | 6/2007 |
| GB | 1044311 | 9/1966 |
| JP | 2004105915 | 4/2004 |
| JP | 2008081730 | 4/2008 |
| WO | WO2004083350 A1 | 9/2004 |
| WO | 2004085579 | 10/2004 |
| WO | 2010043212 | 4/2010 |
| WO | WO2010043213 A1 | 4/2010 |
| WO | 2012068651 | 5/2012 |
| WO | 2014202980 | 12/2014 |

* cited by examiner

PROCESS FOR PRODUCING BIODIESEL AND RELATED PRODUCTS

CROSS REFERENCE TO RELATED APPLICATIONS

This application is a divisional of U.S. Nonprovisional patent application Ser. No. 14/897,936, filed Dec. 11, 2015 and titled, "PROCESS FOR PRODUCING BIODIESEL AND RELATED PRODUCTS," which is a national stage application of Patent Cooperation Treaty application serial number PCT/GB14/051876, filed Jun. 19, 2014, which claimed priority under 35 U.S.C. § 119 to United Kingdom patent application serial numbers 1310960.8, 1310961.6, and 1310962.4, all filed on Jun. 19, 2013, the disclosures of each of the foregoing applications are incorporated herein by reference.

FIELD OF THE INVENTION

This invention relates to a process for producing biodiesel and related products. The invention also relates to a process for producing precursors and/or feedstock materials for producing biodiesel and related products.

BACKGROUND OF THE INVENTION

The term "biodiesel" is used to refer to vegetable or animal fat, oil or grease derived diesel, consisting of long-chain alkyl methyl (ethyl or propyl) esters. Biodiesel is distinct from petroleum diesel (also known as petrodiesel or petroleum derived diesel), which is a specific fractional distillate of petroleum fuel oil.

Biodiesel is typically produced from a variety of feedstocks, including edible and non-edible fats and oils. Fats are triglycerides (triesters of glycerol and any of several fatty acids), and may be either solid or liquid at room temperature. Oils are neutral, non-polar molecules with a high hydrocarbon content. Greases are semisolid lubricants which generally consist of a soap emulsified with mineral or vegetable oil. Greases can be of natural origin, and can be either vegetable or animal derived.

Many of these feedstock fats and oils have high purity, and therefore can be easily converted to biodiesel in a predictable way using known processes and known reaction conditions. However, in general pure feedstocks are more costly, the feedstocks having other potential uses.

There is also available a variety of poor quality and less pure sources of fats and oils (and greases), which can potentially be used to produce biodiesel. However, impure feedstocks are generally more problematic, leading to unpredictable reaction conditions and a less pure, less predictable biodiesel product.

Fuels are required to have a certain degree of purity in order to be usable. For example, biodiesel needs to have a certain purity or FAME (fatty acid methyl ester) value in order to be usable in engines or the like. Current legislation (EN 14214) states that in order to be suitable for use in engines, biodiesel must have a minimum ester content of 96.5%. In general, the starting material used has a large impact on the quality of the biodiesel obtained.

Therefore, due to the impure and unpredictable nature of poor quality feedstocks, it has not been practicable to use such feedstocks as a source of fats and oils (and greases) for producing fuels such as biodiesel.

In addition, existing processes for producing biodiesel are lengthy, and it would be impracticable to increase the throughput time for the production of biodiesel from a feedstock. Furthermore, it would be beneficial to reduce the time taken for the existing biodiesel production process.

It is an object of the present invention to overcome or mitigate at least some of the problems of the prior art.

SUMMARY OF THE INVENTION

According to a first aspect of the invention there is provided a process for producing biodiesel from a mixture, said process comprising the steps of:

(i) providing the mixture to a trans-esterification reaction vessel;

(ii) introducing trans-esterification conditions to the trans-esterification reaction vessel;

(iii) trans-esterifying the triglycerides in the mixture; and (iv) providing a first purification of the trans-esterified mixture;

wherein the first purification of the trans-esterified mixture comprises spraying an aqueous solution, optionally water, onto the surface of the mixture in the trans-esterification reaction vessel, the aqueous solution percolating the mixture and facilitating the removal of impurities therefrom.

The process may comprise the further step of heating the mixture to a reaction temperature for trans-esterification.

The process may comprise the further step of maintaining the mixture at a reaction temperature for trans-esterification.

The trans-esterification reaction temperature may be between approximately 48° C. and approximately 62° C., optionally between approximately 52° C. and approximately 58° C., optionally approximately 55° C.

The amount of free fatty acids (FFAs) in the mixture before trans-esterification may be approximately 3% by weight or less.

Free fatty acid(s) are commonly referred to by the acronym FFA(s), and the terms "FFA" and "FFAs" are used herein in reference to "free fatty acid" and "free fatty acids" respectively.

The step of introducing trans-esterification conditions may comprise adding a trans-esterification catalyst, optionally base, and an alcohol, optionally methanol, to the reaction vessel.

The trans-esterification catalyst may be a methoxide or a suitable salt thereof, optionally from approximately 12% by weight to approximately 14% by weight methoxide, optionally from approximately 12.5% by weight to approximately 13% by weight methoxide.

The mass of trans-esterification catalyst used relative to the % by weight FFAs in the mixture after esterification may be from approximately 1,000 kg per % by weight FFAs to approximately 1,500 kg per % by weight FFAs, optionally from approximately 1,100 kg per % by weight FFAs to approximately 1,450 kg per % by weight FFAs.

The trans-esterification step may comprise:

(i) a first trans-esterification step; and (ii) a second trans-esterification step.

In the first trans-esterification step the mass of trans-esterification catalyst used relative to the % by weight FFAs in the mixture after esterification may be from approximately 1,000 kg catalyst per % by weight FFAs to approximately 1,500 kg catalyst per % by weight FFAs, optionally from approximately 1,100 kg catalyst per % by weight FFAs to approximately 1,450 kg catalyst per % by weight FFAs.

In the second trans-esterification step the mass of trans-esterification catalyst used relative to the % by weight FFAs in the mixture after esterification may be from approximately 550 kg catalyst per % by weight FFAs to approximately 650 kg catalyst per % by weight FFAs, optionally approximately 500 kg catalyst per % by weight FFAs.

The first purification step may be carried out at a temperature of between approximately 47° C. and approximately 61° C., optionally between approximately 51° C. and approximately 57° C., optionally approximately 54° C.

The process may comprise the further step after trans-esterification of separation of a phase comprising impurities from the mixture, said separation comprising spraying an acid solution, optionally a phosphoric acid solution, onto the surface of the mixture in the trans-esterification reaction vessel, the acid solution percolating the mixture and facilitating the removal of impurities therefrom.

The separation step may be carried out at a temperature of between approximately 48° C. and approximately 62° C., optionally between approximately 52° C. and approximately 58° C., optionally approximately 55° C.

The acid solution in the separation step may be from approximately 1.0% by weight acid to approximately 1.8% by weight acid, optionally from approximately 1.2% by weight acid to approximately 1.6% by weight acid, optionally approximately 1.4% by weight acid.

The separation step may be performed before the first purification step.

The process may comprise the further step of a second purification of the trans-esterified mixture.

The second purification step may comprise spraying an acid solution, optionally a phosphoric acid solution, onto the surface of the mixture in the trans-esterification reaction vessel, the acid solution percolating the mixture and facilitating the removal of impurities therefrom.

The second purification step may be carried out at a temperature of between approximately 47° C. and approximately 61° C., optionally between approximately 51° C. and approximately 57° C., optionally approximately 54° C.

The acid solution in the second purification step may be from approximately 0.8% by weight acid to approximately 1.4% by weight acid, optionally from approximately 1.0% by weight acid to approximately 1.6% by weight acid, optionally approximately 1.2% by weight acid.

The second purification step may be performed after the first purification step.

The process may comprise the further step of a third purification of the trans-esterified mixture.

The third purification step may comprise spraying an aqueous solution, optionally water, onto the surface of the mixture in the trans-esterification reaction vessel, the aqueous solution percolating the mixture and facilitating the removal of impurities therefrom.

The third purification step may be carried out at a temperature of between approximately 47° C. and approximately 61° C., optionally between approximately 51° C. and approximately 57° C., optionally approximately 54° C.

The third purification step may be performed after the second purification step.

The process may comprise the further step of distilling the mixture after purification, said distillation process configured to remove sulphur and/or sulphur containing materials from the mixture.

The distillation step may comprise:
(i) a first distillation; and
(ii) a second distillation.

The distillation may be under vacuum, optionally at a pressure of from approximately 0.1 millibar (10 Pa) to approximately 3 millibar (300 Pa).

The first distillation step may comprise injecting steam at a pressure of from approximately 3.5 bar (350 kPa) to approximately 9 bar (900 kPa).

The second distillation step may comprise injecting steam at a pressure of from approximately 4.5 bar (450 kPa) to approximately 11 bar (1,100 kPa).

The impurities may be selected from one or more of group consisting of: glycerides, glycerol, methanol, water, salts, acids, bases, condensed volatile compounds and soaps.

The process may comprise the further step of removing the impurities from the mixture.

The process may comprise the further step of isolating one or more materials from the impurities, said isolated materials selected from one or more of the group consisting of: glycerides, glycerol, methanol and FFAs.

The isolated material may be reused in the process or a subsequent process for producing biodiesel.

The process may comprise the additional step of esterifying the mixture before trans-esterifying the mixture, said esterification process comprising the steps of:
(i) providing at least a first portion of the mixture to at least a first esterification reaction vessel;
(ii) heating the first portion of the mixture to a reaction temperature for esterification;
(iii) introducing esterification conditions to the first esterification reaction vessel;
(iv) stopping the heating of the first portion of the mixture;
(v) recirculating the first portion of the mixture by removing it from the first esterification reaction vessel and returning it to the first esterification reaction vessel; and
(vi) esterifying FFAs in the first portion of the mixture;
wherein the recirculation of the first portion of the mixture is configured to maintain a reaction temperature suitable for esterification of the FFAs in the first portion of the mixture.

Optionally there is provided two or more esterification reaction vessels, said process comprising the further steps of:
(i) providing at least a second portion of the mixture to at least a second esterification reaction vessel;
(ii) heating the second portion of the mixture to a reaction temperature for esterification;
(iii) introducing esterification conditions to the second esterification reaction vessel;
(iv) stopping the heating of the second portion of the mixture;
(v) recirculating the second portion of the mixture by removing it from the second esterification reaction vessel and returning it to the second esterification reaction vessel; and
(vi) esterifying the FFAs in the second portion of the mixture;
wherein the recirculation of the second portion of the mixture is configured to maintain a reaction temperature suitable for esterification of the FFAs in the second portion of the mixture.

The esterification of the first portion of the mixture and the esterification of the second portion of the mixture may be at least partly concurrent.

The amount of FFAs in the mixture may be reduced to approximately 3% by weight or less.

The esterification reaction temperature may be between approximately 71° C. and approximately 76° C., optionally between approximately 72° C. and approximately 75° C., optionally approximately 73.5° C.

The mixture may comprise between approximately 10% and approximately 20% by weight FFAs, optionally between approximately 10% and approximately 15% by weight FFAs, optionally between approximately 13% and approximately 15% by weight FFAs, optionally approximately 14% by weight FFAs before esterification.

Introducing esterification conditions may comprise adding an esterification catalyst, optionally an acid, and an alcohol, optionally methanol, to the reaction vessel.

The esterification catalyst may be sulphuric acid, optionally 96% sulphuric acid.

The mass of esterification catalyst used relative to the % by weight FFAs in the mixture before esterification may be from approximately 26 kg per % by weight FFAs to approximately 32 kg per % by weight FFAs.

According to a second aspect of the invention there is provided a biodiesel composition obtainable, obtained or directly obtained by the process of the first aspect.

According to a third aspect of the invention there is provided a fuel comprising the biodiesel composition of the second aspect.

According to a fourth aspect of the invention there is provided a fuel blend comprising the biodiesel composition of the third aspect and a petroleum diesel.

According to a fifth aspect of the invention these is provided the use of the purified mixture prepared by the process of the first aspect in the preparation of a fuel, the fuel optionally being biodiesel.

According to a sixth aspect of the invention there is provided a process for esterifying a mixture comprising free fatty acids (FFAs), said process comprising the steps of:

(i) providing at least a first portion of the mixture to at least a first reaction vessel;

(ii) heating the first portion of the mixture to a reaction temperature for esterification;

(iii) introducing esterification conditions to the first reaction vessel;

(iv) stopping the heating of the first portion of the mixture;

(v) recirculating the first portion of the mixture by removing it from the first reaction vessel and returning it to the first reaction vessel; and (vi) esterifying the FFAs in the first portion of the mixture;
wherein the recirculation of the first portion of the mixture is configured to maintain a reaction temperature suitable for esterification of the FFAs in the first portion of the mixture.

Optionally there is provided two or more reaction vessels, said process comprising the further steps of:

(i) providing at least a second portion of the mixture to at least a second reaction vessel;

(ii) heating the second portion of the mixture to a reaction temperature for esterification;

(iii) introducing esterification conditions to the second vessel;

(iv) stopping the heating of the second portion of the mixture;

(v) recirculating the second portion of the mixture by removing it from the second reaction vessel and returning it to the second reaction vessel; and (vi) esterifying the FFAs in the second portion of the mixture;
wherein the recirculation of the second portion of the mixture is configured to maintain a reaction temperature suitable for esterification of the FFAs in the second portion of the mixture.

The esterification of the first portion of the mixture and the esterification of the second portion of the mixture may be at least partly concurrent.

The amount of FFAs in the mixture may be reduced to approximately 3% by weight or less.

The reaction temperature may be between approximately 71° C. and approximately 76° C., optionally between approximately 72° C. and approximately 75° C., optionally approximately 73.5° C.

The mixture may comprise between approximately 10% and approximately 20% by weight FFAs, optionally between approximately 10% and approximately 15% by weight FFAs, optionally between approximately 13% and approximately 15% by weight FFAs, optionally approximately 14% by weight FFAs before esterification.

Introducing esterification conditions may comprise adding an esterification catalyst, optionally an acid, and an alcohol, optionally methanol, to the reaction vessel.

The esterification catalyst may be sulphuric acid, optionally 96% sulphuric acid.

The mass of esterification catalyst used relative to the % by weight FFAs in the mixture before esterification may be from approximately 26 kg catalyst per % by weight FFAs to approximately 32 kg catalyst per % by weight FFAs.

According to a seventh aspect of the invention there is provided purified mixture obtainable, obtained or directly obtained by the process of the sixth aspect.

According to an eighth aspect of the invention there is provided a biodiesel composition obtainable, obtained or directly obtained from the purified mixture of the process of the sixth aspect.

According to a ninth aspect of the invention there is provided a fuel comprising the biodiesel composition of the eighth aspect.

According to a tenth aspect of the invention there is provided a fuel blend comprising the biodiesel of the eighth aspect and a petroleum diesel.

According to an eleventh aspect of the invention there is provided the use of the purified mixture prepared by the process of the sixth aspect in the preparation of a fuel, the fuel optionally being biodiesel.

BRIEF DESCRIPTION OF THE DRAWINGS

Embodiments of the invention will now be described, by way of example only, with reference to the drawings, in which.

DETAILED DESCRIPTION

Figure 2:
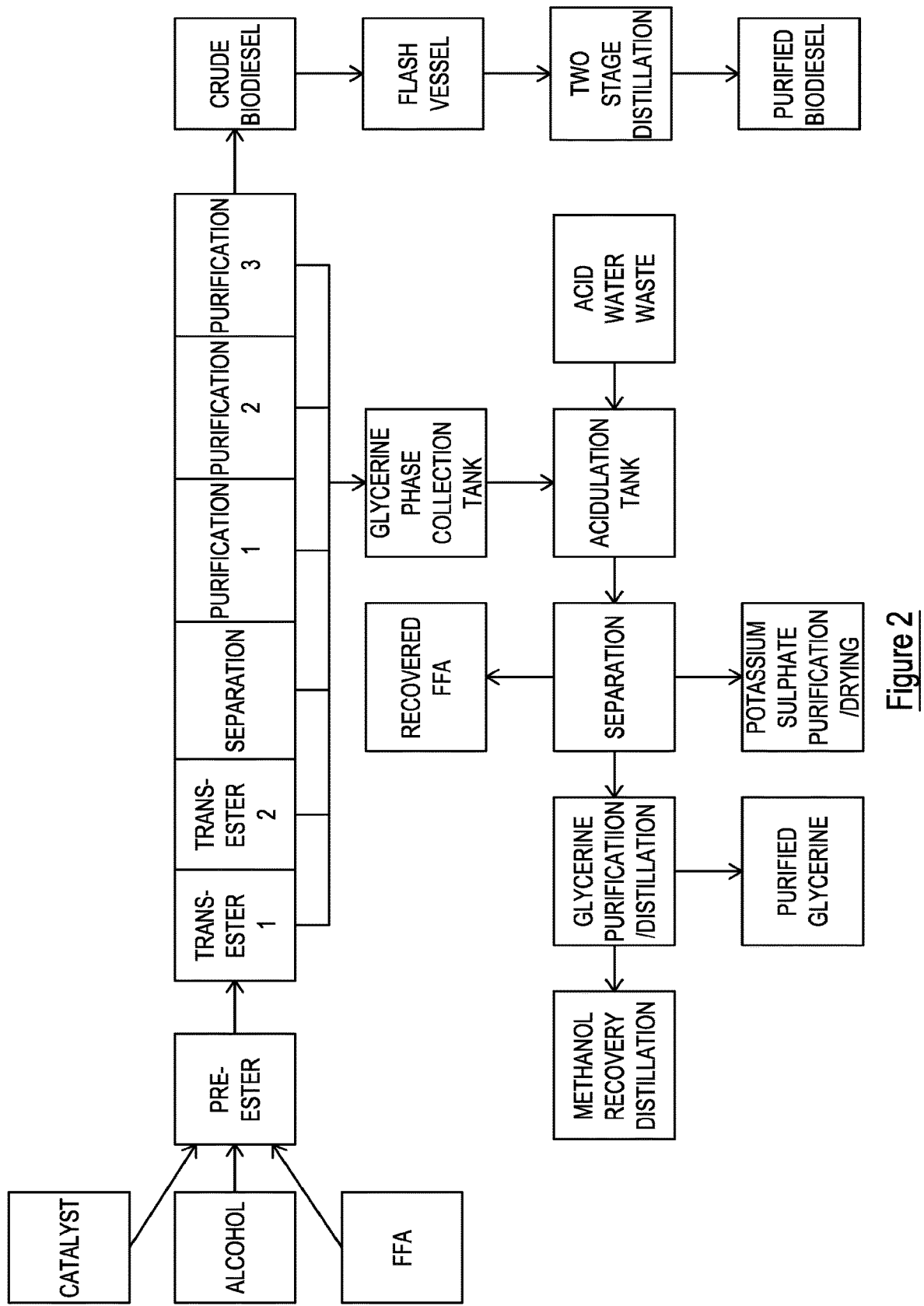
FIG. 2 is a flow diagram which illustrates a process in accordance with one embodiment of the invention.

The biodiesel production process is broken down into two areas, namely esterification (referred to as pre-esterification) and trans-esterification. The processes as further described below are summarised in the flow diagram of FIG. 2.

The processes described are based on approximately 38 tonnes of feedstock (including recovered FFAs) being used.

Pre-Esterification

Pre-esterification is a preconditioning step that produces useable oil for the trans-esterification process. It involves the catalysed esterification of free fatty acids (FFAs) with an alcohol to provide a fatty acid ester.

Figure 1:
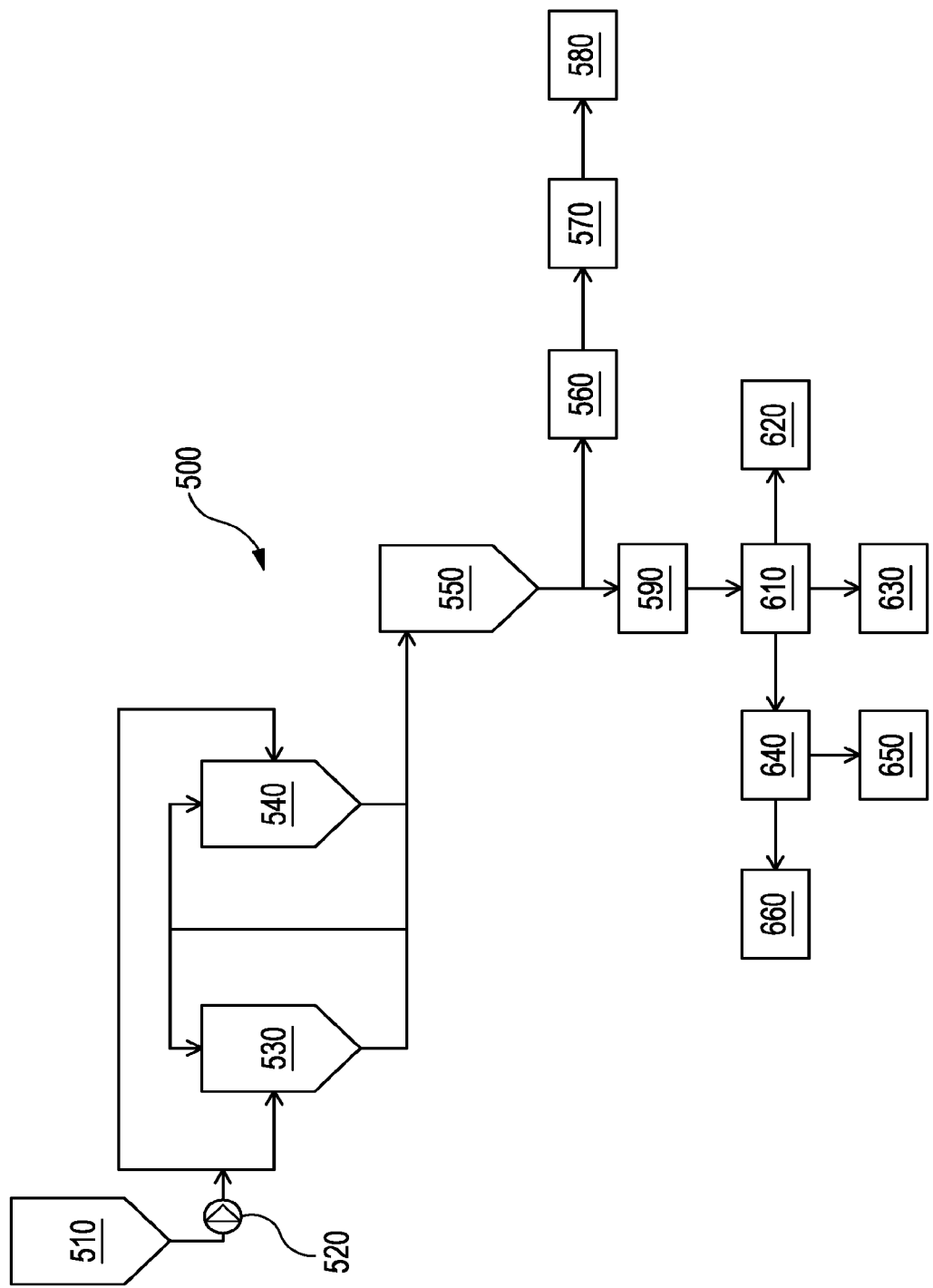
FIG. 1 is schematic diagram of a process in accordance with one embodiment of the invention.

Referring to FIG. 1, there is shown at 100 an apparatus for producing biodiesel. The apparatus comprises a feedstock tank 10 from which tallow (animal fat), which comprises FFAs, and recovered FFAs from the by-product stream of an earlier biodiesel production process, are pumped via pump

20 into a first pre-esterification reactor 30. The total amount of FFAs in the feedstock is typically between 10% by weight and 20% by weight. Under normal operation conditions, the combined amount of FFAs (i.e., when tallow and recovered FFAs are combined) is 10% by weight to 15% by weight, but may also be 13% by weight to 15% by weight. In one embodiment, the total amount of FFAs in the feedstock is 14% by weight.

100 kg of methanol (an alcohol) per tonne of feedstock is then added to the feedstock in the first pre-esterification reactor 30, followed by the addition of 96% by weight sulphuric acid (an esterification catalyst). A range of methanol can be used, varying between 80 kg and 120 kg per tonne of feedstock, and usually between 90 kg and 110 kg per tonne of feedstock. The so-formed mixture is then heated for at least 90 minutes with agitation to a reaction temperature of approximately 73.5° C. The temperature can be between approximately 71° C. and 76° C., and is typically is from between 72° C. and 75° C.

Once the reaction temperature has been reached in the first pre-esterification reactor 30, the mixture is removed from and then returned to the first pre-esterification reactor 30 by recirculation of the mixture such that the reaction temperature is maintained. The recirculation and reaction continues with agitation for approximately 150 minutes, which ensures that the reaction is complete. This so-formed mixture is then allowed to settle for 90 minutes before the water phase is removed.

Once the reaction temperature is reached in the first pre-esterification reactor 30, the feedstock is diverted to a second pre-esterification reactor 40.

100 kg of methanol (an alcohol) per tonne of feedstock is then added to the feedstock in the second pre-esterification reactor 40, followed by the addition of 96% by weight sulphuric acid (an esterification catalyst). A range of methanol can be used, varying between 80 kg and 120 kg per tonne of feedstock, and usually between 90 kg and 110 kg per tonne of feedstock. The so-formed mixture is then heated for at least 90 minutes with agitation to a reaction temperature of approximately 73.5° C. The temperature can be between approximately 71° C. and 76° C., and is typically is from between 72° C. and 75° C.

Once the reaction temperature has been reached in the second pre-esterification reactor 40, the mixture is removed from and then returned to the second pre-esterification reactor 40 by recirculation of the mixture such that the reaction temperature is maintained. The recirculation and reaction continues with agitation for approximately 150 minutes, which ensures that the reaction is complete. This so-formed mixture is then allowed to settle for 90 minutes before the water phase is removed.

The amount of pre-esterification catalyst used is from approximately 26 kg catalyst per % by weight FFAs to approximately 32 kg catalyst per % by weight FFAs.

The quality of the feedstock may deviate on a day to day basis, which can have a significant impact on the following steps of the biodiesel production process to the extent that in known prior art processes such steps may not be viable. For example, if too many impurities are present this can prevent different phases from being separated and/or this can lead to a very poor quality end product.

Thus, fluctuations in FFA content must be taken into account to establish the amount of catalyst that is required to achieve a feedstock suitable for further processing (i.e., suitable for trans-esterification). A suitable endpoint may be when the total amount of FFAs in the mixture is reduced to 3% by weight or less. The inventors have found that a range of pre-esterification catalyst of from approximately 26 kg catalyst per % by weight FFAs to approximately 32 kg catalyst per % by weight FFAs enables a successful pre-esterification to take place.

The pre-esterification process outlined above enables two pre-esterification reactions to take place at least partly concurrently. In particular, once the contents of a pre-esterification reactor reach the reaction temperature, the heat input is removed. The contents of the pre-esterification reactor are then recirculated, the residual heat generated by the reaction enabling the reaction to continue to completion without further external heat being applied. Removing the heat input from one pre-esterification reactor enables a further reaction in another separate pre-esterification reactor to be initiated almost immediately. These improvements reduce the time taken for the pre-esterification process by at least 120 minutes, as compared with using only one pre-esterification reactor of equivalent size. Thus, the process outlined provides a significant improvement in the speed of throughput. Furthermore, the process outlined uses less energy than known pre-esterification processes, due to the use of residual heat of reaction and recirculation of the reaction mixture to maintain the reaction temperature.

Trans-Esterification

The trans-esterification process exchanges the R group on an ester for the R group from an alcohol. In the biodiesel production process it is used to convert triglycerides to fatty acid methyl esters.

Referring once more to FIG. 1, the mixture from the pre-esterification reactors 30, 40 is transferred to a trans-esterification reactor (reaction vessel) 50. The mixture in the trans-esterification reactor 50 is agitated, and recovered methyl ester is added. The recovered methyl ester is obtained later in the process from the separation and purification of the by-products.

2,900 kg of potassium methoxide and 2,500 kg of methanol are added to the mixture in the trans-esterification reactor 50, and the reaction temperature is adjusted to approximately 55° C. The amount of methanol may vary between approximately 2,000 kg and 3,000 kg. The amount of potassium methoxide used above is based on 2% by weight of FFAs in the mixture. However the amount used can be between 1,100 kg per % by weight of FFA and 1,500 kg per % by weight of FFA, typically 1,150 kg per % by weight of FFA and 1,450 kg per % by weight of FFA. Also, the reaction temperature is a reaction temperature for trans-esterification and can be between approximately 48° C. and approximately 62° C., and is typically between approximately 52° C. and approximately 58° C.

Where the catalyst is methoxide in methanol, the amount of methoxide is 12% to 14% by weight methoxide, typically 12.5% by weight to 13% by weight methoxide. The conditions described above are trans-esterification conditions and, specifically, are used to trans-esterify triglycerides in the mixture.

Using the amounts of potassium methoxide noted ensures that the reaction mechanism is driven to completion i.e., methyl ester is formed and glycerol is removed. Whilst in this example potassium methoxide catalyst and methanol in excess is used, other suitable methoxides can be used such as, for example, sodium methoxide.

A second trans-esterification is then carried out in the trans-esterification reactor 50 using a smaller quantity of potassium methoxide catalyst (approximately 600 kg) and methanol (approximately 1,000 kg). The amount of potassium methoxide catalyst may be between approximately 550 kg to approximately 650 kg. The amount of methanol may be between approximately 900 kg to approximately 1,100 kg. The second trans-esterification reaction ensures that substantially all of the triglycerides in the mixture are converted to esters, and that substantially all of the glycerol is removed.

The reaction temperature is adjusted to approximately 55° C., and the reaction is run for around 300 minutes. The reaction temperature is a reaction temperature for trans-esterification and can be between approximately 48° C. and approximately 62° C., and is typically between approximately 52° C. and approximately 58° C.

An optional separation step can be used to aid settling, particularly if the aqueous and non-aqueous phases of the mixture prove difficult or very time-consuming to separate. The separation step involves spraying an aqueous solution comprising 1,000 kg of recycled water and 10 kg to 18 kg of 75% by weight phosphoric acid onto the surface of the mixture in the trans-esterification reactor 50 at a temperature of approximately 70° C. The temperature may be between approximately 60° C. and approximately 80° C. The acid solution percolates through the mixture and the contents of the trans-esterification reactor 50 are allowed to settle for 60 minutes before the so-formed aqueous phase is discharged into a glycerine (aqueous) phase collection tank 90. This process removes impurities and better enables separation of soaps.

Based on the amounts stated above, the acid solution used in the separation step is 1.0% by weight acid to 1.8% by weight acid, but can be from 1.2% by weight acid to 1.6% by weight acid, typically 1.4% by weight acid.

The mixture, still in the trans-esterification tank 50, is then subjected to a first purification (washing) step. The first purification step involves adding approximately 500 kg of water to the mixture, and mechanically agitating the mixture combined with the water, before allowing to settle for approximately 100 minutes. The amount of water used may vary between 400 kg and 600 kg. An aqueous solution comprising 250 kg (150 kg to 350 kg can be used) of recycled water at a temperature of 70° C. (a temperature of 60° C. to 80° C. can be used) is then sprayed onto the surface of the mixture in the trans-esterification reactor 50 before allowing to settle for approximately 140 minutes. The water percolates through the mixture and the contents of the trans-esterification reactor 50 are allowed to settle for 60 minutes before the so-formed aqueous phase is discharged into a glycerine (aqueous) phase collection tank 90.

The mixture, still in the trans-esterification tank 50, is then subjected to a second purification (washing) step. The second purification involves spraying an aqueous solution comprising 1,000 kg of heated (recycled) water and 14 kg of 75% by weight phosphoric acid onto the surface of the mixture in the trans-esterification reactor 50. The temperature of the solution is 70° C. (a temperature of 60° C. to 80° C. can be used). The acid solution percolates through the mixture and the contents of the trans-esterification reactor 50 are allowed to settle for 60 minutes before the so-formed aqueous phase is discharged into a glycerine (aqueous) phase collection tank 90. This process removes impurities and neutralises residual potassium soaps.

Based on the amounts stated above, the acid solution used in the second purification (washing) step is 0.8% by weight acid to 1.6% by weight acid, but can be from 1.0% by weight acid to 1.4% by weight acid, typically 1.2% by weight acid.

A further (third) purification (washing) step is applied to the mixture in the trans-esterification reactor 50. The third purification step involves spraying an aqueous solution comprising 500 to 1,000 kg of recycled water at a temperature of 70° C. (a temperature of 60° C. to 80° C. can be used) onto the surface of the mixture in the trans-esterification reactor 50. The water percolates through the mixture and the contents of the trans-esterification reactor 50 are allowed to settle for 60 minutes before the so-formed aqueous phase is discharged into a glycerine (aqueous) phase collection tank 90. This third purification process ensures that the vast majority of impurities, free glycerides and soaps are removed prior to the non-aqueous phase of the mixture (which is now crude biodiesel) entering a flash vessel 60.

The percolation of the aqueous solutions through the mixture in the trans-esterification reactor 50 facilitates the removal of impurities from the mixture. The impurities removed include, for example, the following: glycerides, glycerol, methanol, water, salts, acids, bases, condensed volatile compounds and soaps.

Depending on the feedstock material used, some or all of the separation/purification steps described above are required. The separation/purification steps ensure that the process is not unduly lengthy. For example, in known prior art processes settling problems may be encountered, which can then lead to excessive waiting times for the separation of the aqueous and non-aqueous phases. The separation step described above helps to overcome such settling problems should they occur. Overall, the separation/purification (washing) steps described can reduce by around 5 hours the time taken to obtain crude biodiesel from the trans-esterification process.

The crude biodiesel mixture obtained from the separation/purification steps is provided to the flash vessel 60, where the crude biodiesel (fatty acid methyl ester mixture) is steam treated (steam injection) under vacuum to remove water, volatile compounds, and free glycerides, all of which may impact on the final quality or the operation of the vacuum system in the distillation step which follows.

From the flash vessel 60, the mixture is transferred to a distillation apparatus 70, where remaining impurities (such as glycerides, water and sulphur or sulphur containing materials) are removed under vacuum, the pressure being set to approximately 0.1 millibar (10 Pa) to approximately 3 millibar (300 Pa).

The distillation takes place is two stages. The first stage has the following conditions. Steam is injected at a pressure of from approximately 3.5 bar (350 kPa) to approximately 9 bar (900 kPa).

The second stage has the following conditions. Steam is injected at a pressure of from approximately 4.5 bar (450 kPa) to approximately 11 bar (1,100 kPa).

The product produced from the distillation apparatus is purified biodiesel, which is transferred to biodiesel tank 80.

The purified biodiesel may be used as a fuel, or may be blended with other products to produce a fuel.

Impurities are periodically removed from the process. For example, the aqueous (glycerine containing) phase from the trans-esterification is periodically separated into the glycerine phase tank 90. This aqueous phase may contain glycerol, methanol, water, salts, acids, bases, condensed volatile compounds and soaps, for example.

The aqueous phase is further transferred to an acidulation tank 110 to which acid water waste is added. The aqueous phase is then separated into recovered FFAs (recovered FFA tank 120), potassium sulphate (potassium sulphate tank 130) and glycerine/methanol (glycerine/methanol tank 140). The glycerine methanol is further separated into purified glycerine (purified glycerine tank 150) and recovered methanol (recovered methanol tank 160). The materials isolated from the impurities can be reused in a subsequent process for producing biodiesel.

The improved processes as described herein enable the use of impure and poor quality feedstocks to produce high quality biodiesel. To date, it has been otherwise impracticable to use such feedstocks as a source of fats and oils (and greases) for producing fuels such as biodiesel.

In addition, the improved processes as described herein enable a reduction in the throughput time for the production of biodiesel from a feedstock. This results in an increased amount of biodiesel production, which is of benefit. For example, the present inventors have found that their improved processes enable the production of biodiesel in approximately 7 to 8 hours less than the time taken using existing processes. For the present facility used by the inventors, this represents an additional 38 tonnes of biodiesel produced in a 24 hour period.

While this invention has been described with reference to the sample embodiments thereof, it will be appreciated by those of ordinary skill in the art that modifications can be made to the structure and elements of the invention without departing from the spirit and scope of the invention as a whole.

The invention claimed is:

1. A process for esterifying a mixture comprising between 10% and 20% by weight free fatty acids (FFAs), said process comprising the steps of: (i) providing at least a first portion of the mixture to at least a first reaction vessel; (ii) heating the first portion of the mixture to a reaction temperature for esterification, the reaction temperature being between 71° C. and 76° C.; (iii) introducing esterification conditions to the first reaction vessel, comprising adding an esterification catalyst and an alcohol to the reaction vessel, the esterification catalyst being sulphuric acid; (iv) stopping the heating of the first portion of the mixture; (v) recirculating the first portion of the mixture by removing it from the first reaction vessel and returning it to the first reaction vessel without further external heat being applied; (vi) esterifying the FFAs in the first portion of the mixture; (vii) providing at least a second portion of the mixture to at least a second reaction vessel; (viii) heating the second portion of the mixture to a reaction temperature for esterification, the reaction temperature being between 71° C. and 76° C.; (ix) introducing esterification conditions to the second vessel, comprising adding an esterification catalyst and an alcohol to the reaction vessel, the esterification catalyst being sulphuric acid; (x) stopping the heating of the second portion of the mixture; (xi) recirculating the second portion of the mixture by removing it from the second reaction vessel and returning it to the second reaction vessel without further external heat being applied; and (xii) esterifying the FFAs in the second portion of the mixture; wherein the recirculation of the first portion of the mixture is configured to maintain a reaction temperature suitable for esterification of the FFAs in the first portion of the mixture, the reaction temperature being between 71° C. and 76° C.; wherein the recirculation of the second portion of the mixture is configured to maintain a reaction temperature suitable for esterification of the FFAs in the second portion of the mixture, the reaction temperature being between 71° C. and 76° C.; and wherein the mass of esterification catalyst used relative to the % by weight FFAs in the mixture before esterification is from 26 kg catalyst per % by weight FFAs to 32 kg catalyst per % by weight FFAs, such that the amount of FFAs in the mixture is reduced to 3% by weight or less.

2. A process as claimed in claim 1, wherein the esterification of the first portion of the mixture and the esterification of the second portion of the mixture are at least partly concurrent.

3. A process as claimed in claim 1, wherein the reaction temperature is between 72° C. and 75° C.

4. A process as claimed in claim 1, wherein the mixture comprises between 10% and 15% by weight FFAs before esterification.

5. A process as claimed in claim 1, wherein the alcohol is methanol.

6. A process for esterifying a mixture comprising between 10% and 20% by weight free fatty acids (FFAs), said process comprising the steps of:
(i) providing at least a first portion of the mixture to at least a first reaction vessel;
(ii) heating the first portion of the mixture to a reaction temperature for esterification, the reaction temperature being between 71° C. and 76° C.;
(iii) introducing esterification conditions to the first reaction vessel, comprising adding an esterification catalyst and an alcohol to the reaction vessel, the esterification catalyst being sulphuric acid;
(iv) stopping the heating of the first portion of the mixture;
(v) recirculating the first portion of the mixture by removing it from the first reaction vessel and returning it to the first reaction vessel; and
(vi) esterifying the FFAs in the first portion of the mixture;
(vii) providing at least a second portion of the mixture to at least a second reaction vessel;
(viii) heating the second portion of the mixture to a reaction temperature for esterification, the reaction temperature being between 71° C. and 76° C.;
(ix) introducing esterification conditions to the second vessel, comprising adding an esterification catalyst and an alcohol to the reaction vessel, the esterification catalyst being sulphuric acid;
(x) stopping the heating of the second portion of the mixture;
(xi) recirculating the second portion of the mixture by removing it from the second reaction vessel and returning it to the second reaction vessel; and
(xii) esterifying the FFAs in the second portion of the mixture;
wherein the recirculation of the first portion of the mixture is configured to maintain a reaction temperature suitable for esterification of the FFAs in the first portion of the mixture, the reaction temperature being between 71° C. and 76° C.;
wherein the recirculation of the second portion of the mixture is configured to maintain a reaction temperature suitable for esterification of the FFAs in the second portion of the mixture, the reaction temperature being between 71° C. and 76° C.;
wherein the mass of esterification catalyst used relative to the % by weight FFAs in the mixture before esterification is from 26 kg catalyst per % by weight FFAs to 32 kg catalyst per % by weight FFAs, such that the amount of FFAs in the mixture is reduced to 3% by weight or less; and
wherein the esterification of the first portion of the mixture and the esterification of the second portion of the mixture are at least partly concurrent.

7. A process as claimed in claim 6, wherein the reaction temperature is between 72° C. and 75° C.

8. A process as claimed in claim 6, wherein the mixture comprises between 10% and 15% by weight FFAs before esterification.

9. A process as claimed in claim 6, wherein the alcohol is methanol.

10. A process as claimed in claim 6, wherein the esterification catalyst is 96% sulphuric acid.

* * * * *